United States Patent [19]

Heinze

[11] Patent Number: 5,058,586
[45] Date of Patent: Oct. 22, 1991

[54] CATHETER FOR IMPLANTATION IN THE HEART, HAVING AN INTEGRATED MEASURING PROBE

[75] Inventor: Roland Heinze, Munich, Fed. Rep. of Germany

[73] Assignee: Siemens Aktiengesellschaft, Munich, Fed. Rep. of Germany

[21] Appl. No.: 223,027

[22] Filed: Jul. 22, 1988

[30] Foreign Application Priority Data

Jul. 27, 1987 [DE] Fed. Rep. of Germany ....... 3724845

[51] Int. Cl.⁵ .............................................. A61B 5/14
[52] U.S. Cl. .................................. 128/634; 128/642; 128/786
[58] Field of Search ............... 128/633, 634, 665, 666, 128/642, 419 PG, 419 P, 419 D, 784-786

[56] References Cited

U.S. PATENT DOCUMENTS

| | | | |
|---|---|---|---|
| 3,358,690 | 12/1967 | Cohen | 128/419 PG |
| 3,674,013 | 7/1972 | Polanyl . | |
| 3,729,008 | 4/1973 | Berkovits . | |
| 4,154,247 | 5/1979 | O'Neill . | |
| 4,399,820 | 8/1983 | Wirtzfeld et al. | 128/419 PG |
| 4,567,901 | 2/1986 | Harris | 128/786 |
| 4,750,495 | 6/1988 | Moore et al. | 128/633 |
| 4,763,646 | 8/1988 | Lekholm | 128/419 PG |
| 4,770,177 | 9/1988 | Schroeppel | 128/419 PG |
| 4,777,955 | 10/1988 | Branton et al. | 128/642 |
| 4,815,469 | 3/1989 | Cohen et al. | 128/634 |

FOREIGN PATENT DOCUMENTS 2116047 9/1983 United Kingdom .

Primary Examiner—William E. Kamm
Assistant Examiner—John Hanley
Attorney, Agent, or Firm—Hill, Van Santen, Steadman & Simpson

[57] ABSTRACT

A catheter of the type suitable for implantation in a human heart has a catheter tip and a preset curvature spaced along the catheter a distance from the tip. The catheter includes an integrated measuring probe with a measurement window, the measuring probe and window being disposed between the tip and the preset curvature at respective distances from each so that, given the aforementioned location of the catheter tip, it is insured that the measurement window of the probe will not lie against a wall of the heart, which would degrade the operation of the measuring probe, and moreover insures that the measuring probe and measurement window will be disposed at an optimum location for undertaking the desired measurement.

1 Claim, 2 Drawing Sheets

CATHETER FOR IMPLANTATION IN THE HEART, HAVING AN INTEGRATED MEASURING PROBE

BACKGROUND OF THE INVENTION

1. Field of the Invention

The present invention is directed to a catheter having a integrated measuring probe having a measurement window disposed between a preset curvature of the catheter and the catheter tip.

2. Description of the Prior Art

A catheter having a preset or permanent bend or curvature therein is described in U.S. Pat. No. 3,674,013. This catheter also includes a fiber optics means for measuring blood oxygen in the blood vessels. The fiber optics has a light exit window disposed along a side of the catheter. The light exit window lies inside the preset bend of the catheter, i.e., between the bend and the catheter tip, so as to prevent the light exit window from coming too close to the walls of the blood vessel.

Another catheter having an integrated measuring probe for introduction into the heart is disclosed, for example, in German OS 21 42 983, corresponding to U.S. Pat. No. 3,729,008. In this catheter, the blood oxygen saturation is measured by the measuring probe using reflection oximetry, to control the pacing rate of the pacemaker to which the catheter is connected. Light from a light emitting diode is laterally directed out of the catheter through a window in the catheter wall, and the light reflected by the blood, dependent upon its oxygen saturation, is measured using a phototransistor. This type of measuring probe can supply satisfactory measured results only if the measurement window, i.e., the active surface of the measuring probe, does not lie adjacent a wall of the heart, the heart valves, or the trabeculae. This placement restriction applies not only to probes for undertaking a blood oxygen measurement, but also to other types of measurement probes, for example impedance measurement probes. This known catheter is slightly curved following introduction into the heart, however, it is left to chance as to whether the measurement window of the measuring probe comes to lie inside or outside of the curvature.

A catheter is described in U.S. Pat. No. 4,567,901 having stimulation electrodes for the atrium and ventricle, wherein that portion of the catheter which comes to lie in the atrium has a preset curvature to facilitate positioning of the catheter.

SUMMARY OF THE INVENTION

It is an object of the present invention to provide a catheter having an integrated measuring probe wherein it is insured that the measurement window of the measuring probe will be positioned at a defined region of the atrium upon implantation of the catheter in the heart, and furthermore that this defined position will minimize the accumulation of deposits on the measurement window.

The above object is achieved in accordance with the principles of the present invention in a catheter for implantation in a human heart, the catheter having a preset curvature disposed a distance from the catheter tip, with the measuring probe being disposed between the curvature and the catheter tip at respective distances from each so that when the tip of the catheter comes to lie in the ventricle against the right wall of the heart, the measuring probe will be positioned between the right wall of the heart and the level of the heart valves. This structure assures that the measuring probe will be positioned in the atrium region when introduction of the catheter is completed. The measurement window of the measuring probe is prevented from being placed against a wall of the heart due to the preset curvature. Moreover, measurement of the blood oxygen saturation in the atrium region is assured to be made at the optimum location, because reflection artefacts due to heart valves and trabeculae are avoided.

It has been shown that disposing the measuring probe inside the preset curvature, i.e., between that curvature and the catheter tip, more reliably prevents inadvertent positioning of the measurement window against the heart valves, than does positioning the measuring probe outside of the preset curvature. The catheter described in the aforementioned U.S. Pat. No. 3,674,013 has a curvature in the region of the tip of the catheter which satisfactorily prevents placement of the measurement window against the walls of blood vessels. Given implantation of this known catheter in the heart, however, it is possible that the measurement window could easily lie against a heart valve, if the distance from the tip of the catheter does not insure the sensor position in the atrium. An unambiguous reflection-proof positioning of the measuring probe in a defined region of the atrium is thus not possible using this known device. It is preferable to position a blood oxygen saturation measuring sensor in the atrium roughly midway between the right cardiac wall an the level of the valves, because the mixing of the venous blood from the superior and inferior venae cava is best in this central atrium region. Positioning of the measuring probe inside the present curvature, i.e. in the region of the atrium, permits a more reliable and unambiguous location of the measuring probe in the atrium. Other types of preset curvatures which are disposed more closely to the tip of the catheter, for facilitating insertion of the catheter, may force the catheter toward the pulmonary artery, with the result of the sensor being at the valve level. Such preset curvatures, such as a J-curvature, are substantially fully contained within the ventricle upon the completion of implantation and, given the high elasticity of implantable catheters, do not provide an adequate torque in the atrium region, as does the structure of U.S. Pat. No. 3,674,013. If the probe were to be disposed directly in the curvature, the probe may, upon the completion of implantation, be located excessively close to the cardiac wall, wherein the degree of mixing of the blood is not as good as preceding the heart valve.

The preset curvature can be produced by angling all of the mechanical connections of the measuring probe to the catheter relative to the probe axes.

It is also possible to provide the preset curvature by using an insulating layer for the catheter having such a preset curvature.

The preset curvature thus remains somewhat elastic, thereby facilitating introduction of the catheter into the heart. If the catheter is of the type having a coiled electrical lead, the preset curvature can be produced by casting the lead to the measuring probe with plastic in a curved condition, the plastic having an elastic form fit.

DESCRIPTION OF THE PREFERRED EMBODIMENTS

Figure 1:
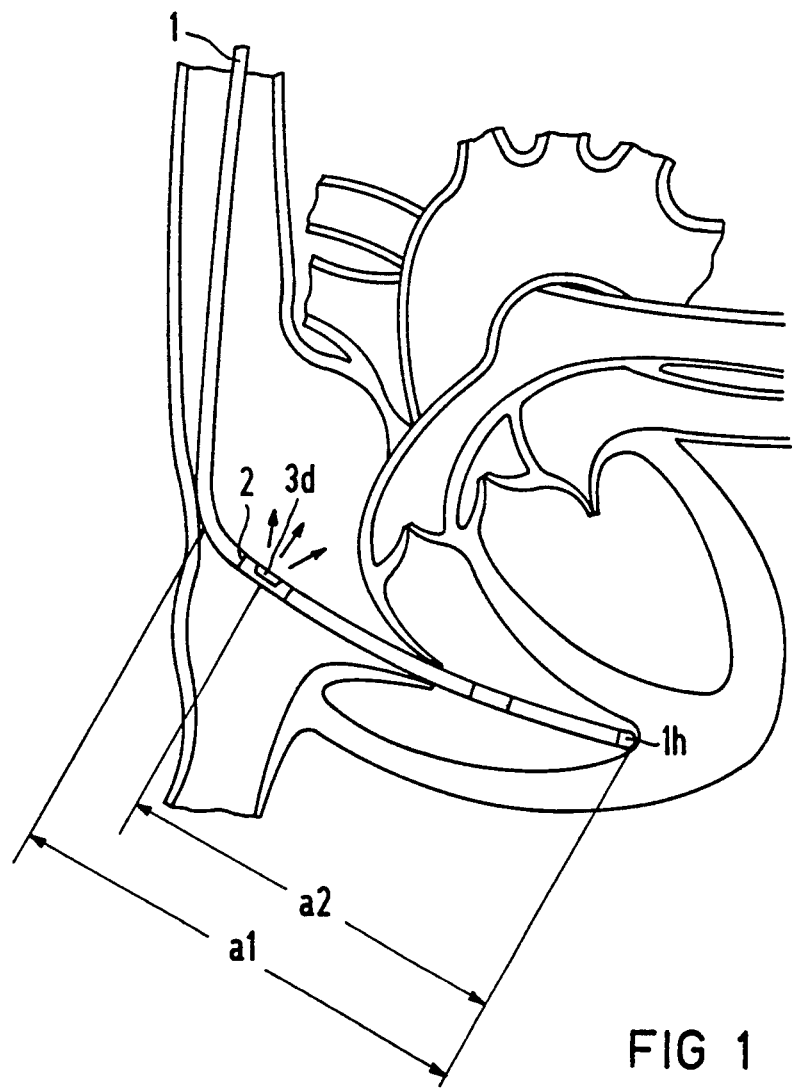
FIG. 1 is a sectional view of a human heart with a catheter constructed in accordance with the principles of the present invention inserted therein.

FIG. 1 shows the placement of a catheter 1 having a stimulation electrode 1h at a distal tip of the catheter introduced into the right ventricle of the heart. The catheter has a preset curvature as shown in FIG. 1 which is set during manufacture of the catheter, so that the stimulation electrode and tip 1h come to lie centrally in the ventricle upon the completion of implantation. A measuring probe having a measurement window 3d is disposed between the preset curvature and the tip 1h, so that when the tip 1h comes to lie as shown in FIG. 1, the measurement window 3d will be disposed in the atrium region, so that it is insured that the measurement window 3d will not be undesirably close to a heart wall. The preset curvature of the catheter optimizes the positioning of the measuring probe 2 because it naturally adapts to the lateral angle of the cardiac muscle relative to the path of the main veins. This is achieved by suitable matching of the distance a1 of the preset curvature from the tip 1h and the distance a2 of the measuring probe 2 to the tip 1h to the anatomy of the heart.

Figure 2:
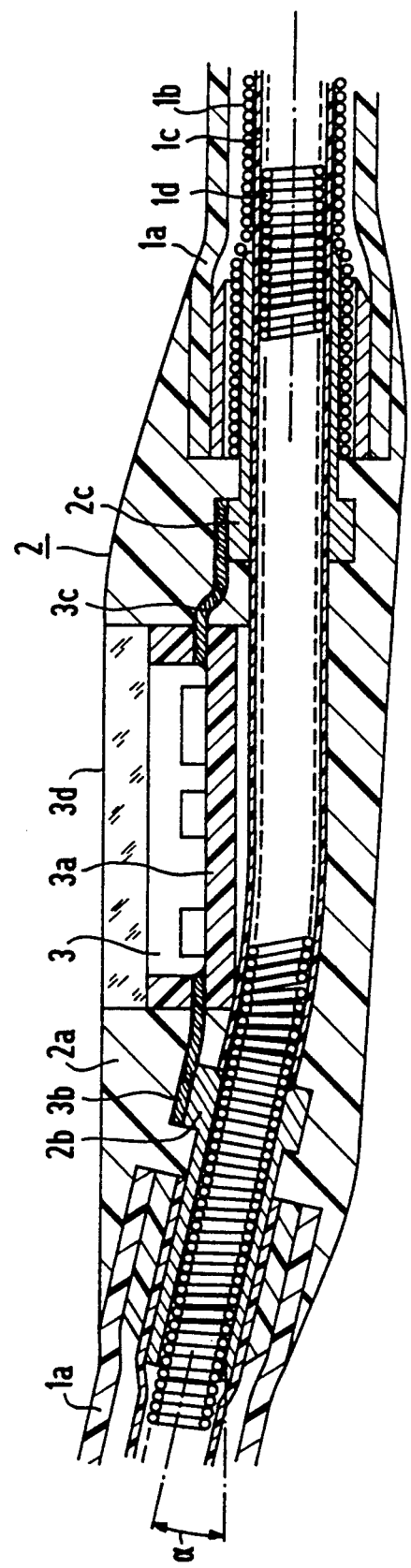
FIG. 2 is a sectional view of a portion of the catheter constructed in accordance with the principles of the present invention in which the measuring probe is disposed.

FIG. 2 shows a sectional view of an exemplary embodiment of a catheter 1 having a curvature disposed so that the measuring probe 2 is inside the curvature. The interior structure of the catheter 1 is designed in a known manner having concentric wire helices 1b and 1d insulated from each other by an internal insulation 1c. The catheter 1 is surrounded by an outer insulation 1a. The measuring probe 2, which in the embodiment of FIG. 2 measures blood oxygen saturation, includes a probe body 2a having connectors 2b and 2c, and the actual measuring sensor 3. The connectors 2b and 2c are disposed at an angle $\alpha$ relative to the probe axis. The inner wire helix 1d is electrically connected to the connector 2b of the measuring probe 2, and leads to the stimulation electrode 1h. The outer wall helix 1b is electrically connected to the connector 2c. The outer insulation 1a is mechanically connected by thermal means to the measuring probe 2 so that the catheter 1 has the same angle relative to the probe axis as do the connectors 2d and 2c.

The measuring sensor 3 in this embodiment consists of a carrier 3a for the optical semiconductor, a glass lens 3d serving as the measurement window, and two electrical terminals 3b and 3c.

Instead of employing a measuring probe having angled connections, other structure may be used to provide the preset curvature of the catheter. For example, one or both of the insulating layers 1a and 1c of the catheter 1 may be provided with a preset curvature during manufacture. A preset curvature can also be achieved by casting one or both of the wire helicies 1b and 1d with plastic while curved, such casting being undertaken with an elastic form fit.

Although modifications and changes may be suggested by those skilled in the art it is the intention of the inventor to embody within the patent warranted hereon all changes and modifications as reasonably and properly come within the scope of his contribution to the art.

I claim as my invention:

1. A device for implantation in a human heart comprising:
    a catheter having a tip;
    means forming a preset curvature in said catheter spaced from said tip; and
    a measuring probe integrated in said catheter between said means for forming a preset curvature and said tip and disposed respective distances from said means for forming a preset curvature and from said tip so that said measuring probe is disposed between the right wall of the heart and the level of the heart valves upon implantation of said catheter in said heart, said measuring probe having a probe axis and said means for forming said preset curvature having mechanical connections for said measuring probe disposed at an angle relative to said probe axis.

* * * * *